United States Patent [19]

VandenBerg

[11] Patent Number: Plant 7,578

[45] Date of Patent: Jul. 2, 1991

[54] CHRYSANTHEMUM PLANT NAMED CREAM BOALDI

[75] Inventor: Cornelis P. VandenBerg, Salinas, Calif.

[73] Assignee: Yoder Brothers, Inc., Barberton, Ohio

[21] Appl. No.: 409,638

[22] Filed: Sep. 18, 1989

[51] Int. Cl.[5] ..... A01H 5/00

[52] U.S. Cl. ..... Plt./78

[58] Field of Search ..... Plt./77, 78

[56] References Cited

U.S. PATENT DOCUMENTS

| | | | |
|---|---|---|---|
| P.P. 4,889 | 9/1982 | van der Knaap | Plt. 78 |
| P.P. 5,226 | 5/1984 | Duffett | Plt. 78 |
| P.P. 5,351 | 11/1984 | Duffett | Plt. 78 |
| P.P. 6,223 | 7/1988 | Hesse | Plt. 78 |
| P.P. 6,613 | 2/1989 | Duffett | Plt. 77 |
| 4,616,099 | 10/1986 | Sparkes | 47/58 |

OTHER PUBLICATIONS

Broertjes et al., 1980, "A mutant of a mutant of a mutant of a . . . Irradiation of progressive radiation-induced mutants in a mutation breeding programme with *Chrysanthemum noufolium*", *Euphytica, 29(1980): 525-530.*

Gosling, S. ed., 1979, "The Chrysanthemum manual", Nat. Chrysanthemum Sec., London, England, pp. 329-336.

Broertjes et al., 1978, "Application of mutation breeding methods in the improvement of vegitatively propagated crops", Elsevier Pub. Co., NY, pp. 162-175.

Searle et al., 1968, "Chrysanthemum the year round", Blanford Press, London, pp. 26-29, 320-327.

Broertjes, 1966, "Mutation breeding of Chrysanthemums", Euphytica, 15(1966): 156-162.

Chan et al., 1966, "Chrysanthemum and rose mutations induced by X-rays", Am. Sec. Hort. Sci., vol. 88(1966): 613-620.

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Cream Boaldi particularly characterized by its flat capitulum form; decorative capitulum type; light yellow ray floret color; diameter across face of capitulum of up to 11 cm at maturity when grown as a pinched disbudded pot mum; uniform eight week photoperiodic flowering response to short days; medium plant height when grown as a pinched pot mum; recommended both as disbudded and spray pot mum; and spreading and prolific branching pattern.

3 Drawing Sheets

The present invention comprises a new and distinct cultivar of Chrysanthemum, botanically known as *Dendranthema grandiflora,* and referred to by the cultivar name Cream Boaldi.

Cream Boaldi, identified as 81-D11B23, is a product of a mutation induction program which had the objective of creating new Chrysanthemum cultivars that would expand the color range of an existing cultivar while retaining all other traits.

Cream Boaldi was discovered and selected by Cornelis P. VandenBerg on May 18, 1987 in a controlled environment in Salinas, Calif. as one flowering plant within a flowering block established as rooted cuttings from stock plants which had been exposed as unrooted cuttings to an X-ray source of 2,000 rads. The irradiated parent was the cultivar Boaldi, disclosed in U.S. Plant Pat. No. 6,613.

The first act of asexual reproduction of Cream Boaldi was accomplished when vegetative cuttings were taken from the initial selection in July of 1987 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Cream Boaldi are firmly fixed and are retained through successive generations of asexual reproduction.

Cream Boaldi has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Cream Boaldi, which, in combination, distinguish this Chrysanthemum as a new and distinct cultivar:

1. Flat capitulum form.
2. Decorative capitulum type.
3. Light yellow ray floret color.
4. Diameter across face of capitulum up to 11 cm at maturity when grown as a pinched disbudded pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Recommended both as disbudded and spray pot mum.
8. Spreading and prolific branching pattern.

The accompanying photographic drawings show typical inflorescence and leaf characteristics of Cream Boaldi, with the colors being as nearly true as possible with illustrations of this type.

Sheet 1 is a color photograph of Cream Boaldi grown as a pinched disbudded pot mum.

Sheet 2 is a black and white photograph of three views of the inflorescence of Cream Boaldi.

Sheet 3 is a black and white photograph showing the upper and under sides of the leaves of Cream Boaldi at three stages of development (mature, intermediate and immature).

Of the commercial cultivars known to the inventor, the most similar in comparison to Cream Boaldi is the parent cultivar Boaldi. All traits of Cream Boaldi are similar to those of Boaldi, except the color of the ray florets. The colors of the ray florets of Cream Boaldi is light yellow, as contrasted with the pure white ray florets of Boaldi.

In the following description color references are made to The Royal Horticultural Society Color Chart. The color values were determined on plant material grown as a pinched disbudded pot mum in Salinas, Calif. on June 8, 1989.

Classification:

*Botanical.*—*Dendranthema grandiflora* cv Cream Boaldi.

*Commercial.*—Decorative disbud and spray pot mum.

INFLORESCENCE

A. Capitulum:

*Form.*—Flat.

*Type.*—Decorative.

*Diameter across face.*—Up to 11 cm at maturity when grown as a pinched disbudded pot mum.

B. Corolla of ray florets:

*Color (general tonality from a distance of three meters).*—Light yellow.

*Color (upper surface).*—2D to 4D.

*Color (under surface).*—2D to 4D.

*Shape.*—Flat, oblong.

C. Corolla of disc florets:

*Color (mature).*—Closest to 154B.

*Color (immature).*—Closest to 144B.

D. Reproductive organs:

*Androecium.*—Present on disc florets only; scant pollen.

*Gynoecium.*—Present on both ray and disc florets.

PLANT

A. General appearance:

*Height.*—Medium; 25 to 35 cm as a pinched pot mum with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Lobed and serrated.

I claim:

1. A new and distinct Chrysanthemum plant named Cream Boaldi, as described and illustrated.

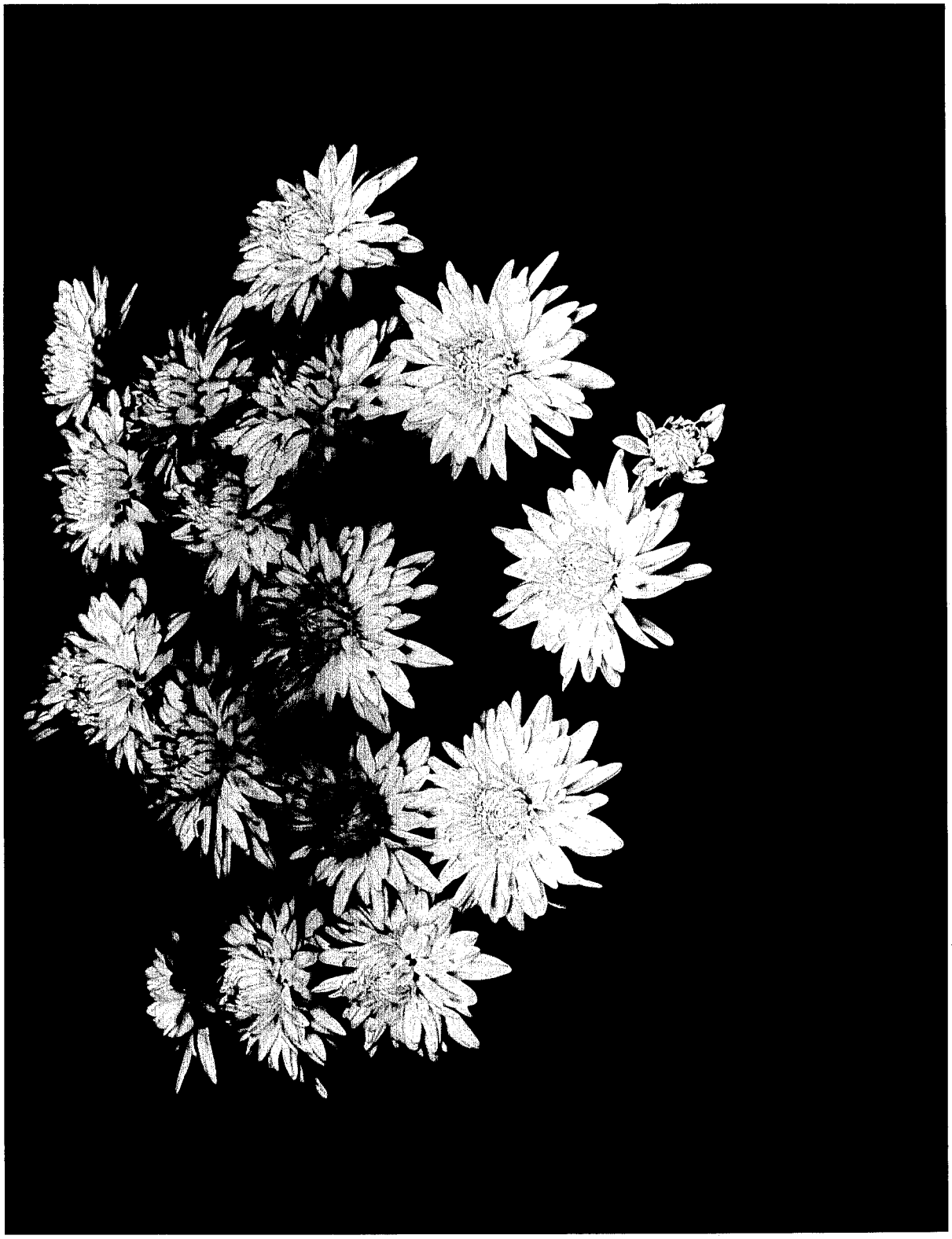

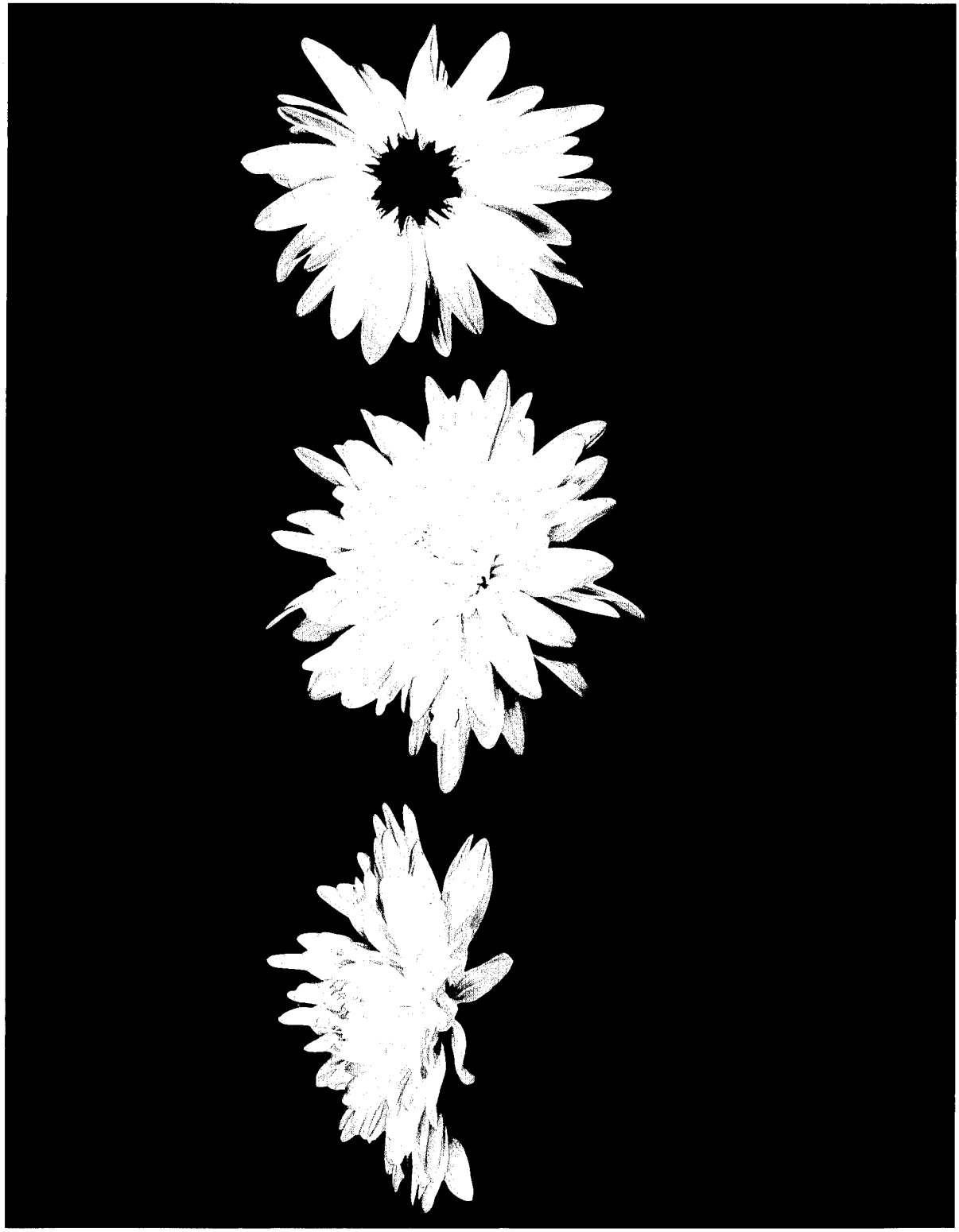

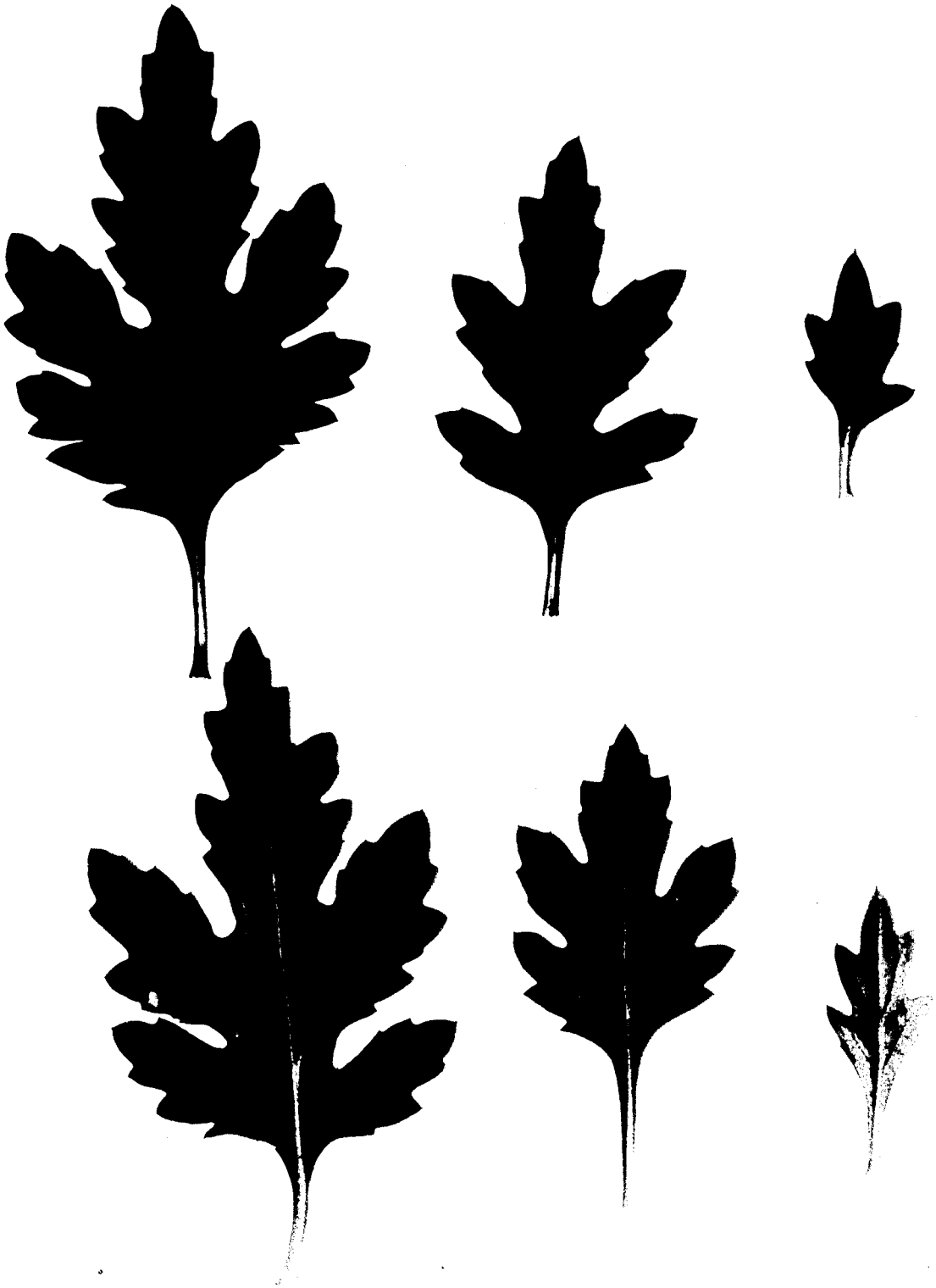

* * * * *